United States Patent [19]

Augelli-Szafran et al.

[11] Patent Number: 5,118,697

[45] Date of Patent: Jun. 2, 1992

[54] CYCLIC BETA-KETOAMIDE ACAT INHIBITORS

[75] Inventors: Corinne E. Augelli-Szafran, Ypsilanti; Bharat K. Trivedi, Farmington Hills, both of Mich.

[73] Assignee: Warner-Lambert Company, Morris Plains, N.J.

[21] Appl. No.: 665,064

[22] Filed: Mar. 6, 1991

[51] Int. Cl.$^5$ .................. A61K 31/44; C07D 213/50
[52] U.S. Cl. .................. 514/357; 546/256; 546/265; 546/331; 546/333; 546/335; 546/337; 548/510; 560/12; 562/426; 562/435; 562/440; 564/74; 564/163; 564/167; 564/171; 564/181; 564/184; 564/185
[58] Field of Search ............ 546/331, 337, 333, 335; 514/357

[56] References Cited

U.S. PATENT DOCUMENTS

| | | | |
|---|---|---|---|
| 3,510,492 | 5/1970 | Semuszkovicz et al. | 260/293 |
| 3,600,360 | 8/1971 | Bukac et al. | 260/78 L |
| 4,075,217 | 2/1978 | Gelotte et al. | 546/337 |
| 4,454,324 | 7/1984 | Madding et al. | 546/337 |

OTHER PUBLICATIONS

Jäger, Chem. Ber. 105, 1972, pp. 137–149.
Chem. Abstract 76:99585y, Chem. Ber. 1972, 105(1), 137–49.
Chem. Abstract 77:101362q, J. Chem. Soc., Perkin Trans. 1, 1972, (17), 2119–21.

Primary Examiner—C. Warren Ivy
Assistant Examiner—James H. Turnipseed
Attorney, Agent, or Firm—Ruth H. Newtson

[57] ABSTRACT

Novel cyclic beta-ketoamides which contain an aryl moiety having utility as blood cholesterol lowering agents rendering them useful in the treatment of atherosclerosis.

8 Claims, No Drawings

CYCLIC BETA-KETOAMIDE ACAT INHIBITORS

BACKGROUND OF THE INVENTION

This invention relates to chemical compounds having pharmacological activity, to pharmaceutical compositions which include these compounds, and to a pharmaceutical method of treatment. More particularly, this invention concerns certain cyclic beta-ketoamide compounds which inhibit the enzyme acyl-coenzyme A:-cholesterol acyltransferase (ACAT), pharmaceutical compositions containing these compounds, and a method of treating hypercholesterolemia and atherosclerosis. This invention also describes novel intermediates useful in preparing the pharmaceutically active compounds of this invention.

In recent years the role which elevated blood plasma levels of cholesterol plays in pathological conditions in man has received much attention. Deposits of cholesterol in the vascular system have been indicated as causative of a variety of pathological conditions, including coronary heart disease.

Initially, studies of this problem were directed toward finding therapeutic agents which would be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

INFORMATION DISCLOSURE STATEMENT

U.S. Pat. No. 3,600,360, issued Aug. 17, 1971, discloses the following compounds as intermediates in the manufacture of polyamides:

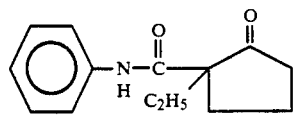

U.S. Pat. No. 3,510,492, issued May 5, 1970, describes compounds of the following general formula which are intermediates in the preparation of 2-anilino and 2-anilinomethyl cycloalkylamines and are disclosed as antidiabetic agents:

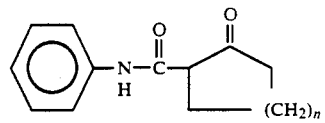

wherein n can be 1 to 4. No specific example of such a compound is disclosed.

Chemical abstracts indexed the following two compounds, giving them the registry numbers set forth below. The abstract is CA 76:99585Y, Chem. Ber. 1972, 105(1), 137–49.

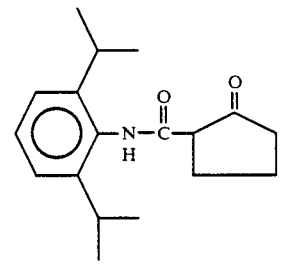

RN35563-33-8

RN35563-32-7

Other compounds disclosed in Chem. Ber. 1972, 105(1), 137–49 are the following:

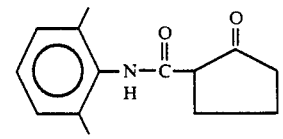

wherein R is phenyl, 2-methylphenyl, 3-methylphenyl, 4-methylphenyl, 2-isopropylphinyl, 4-methoxyphenyl, 4-ethoxyphenyl, 2-chlorophenyl, 3-chlorophenyl, 4-chlorophenyl, 2,3-dichlorophenyl, 2,4-dichlorophenyl, 2,5-dichlorophenyl, 3,4-dichlorophenyl, 2,4,5-trichlorophenyl, 2-chloro-5-trifluoromethylphenyl, 4-chloro-2-trifluoromethylphenyl, 3,5-di(trifluoromethyl)phenyl, 2-chloro-4-nitrophenyl, and 4-nitro-2-methylphenyl. No use is given for any of these compounds.

Chemical Abstracts indexed the following compounds giving them the registry numbers set forth below. The abstract is CA 77:101362q, J. Chem. Soc., Perkin Trans. 1, 1972, (17), 2119–21. These compounds are intermediates and no pharmacological use is described therefor.

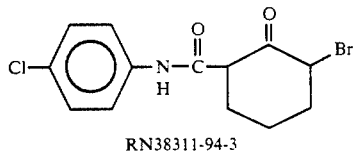
RN38311-94-3

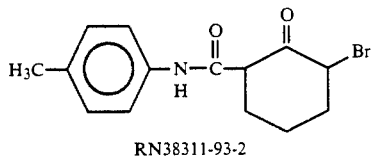
RN38311-93-2

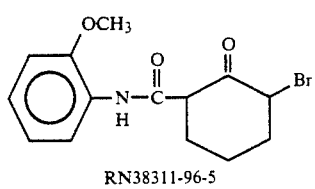
RN38311-96-5

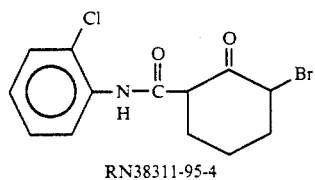
RN38311-95-4

No use is described for these compounds.

SUMMARY OF THE INVENTION

Compounds of the following general Formula I have acyl-coenzyme A:cholesterol acyltransferase (ACAT) inhibitory activity rendering them useful in lowering blood cholesterol levels and serving to treat atherosclerosis:

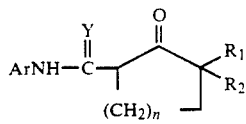

Formula I wherein Y is oxygen or sulfur;
wherein Ar is selected from:
(a) phenyl which is unsubstituted or is substituted with from 1 to 3 substituents selected from:
alkyl having from 1 to 6 carbon atoms and which is straight or branched,
alkoxy having from 1 to 6 carbon atoms and which is straight or branched,
phenoxy,
hydroxy,
fluorine,
chlorine,
bromine,
nitro,
trifluoromethyl,
—COOH,
—COO alkyl wherein alkyl has from 1 to 4 carbon atoms,
—$NR_3R_4$ wherein $R_3$ and $R_4$ are independently hydrogen or alkyl of from 1 to 4 carbon atoms;
wherein n is an integer of from 0 to 3;
wherein $R_1$ is selected from
(a) hydrogen;

(b) phenyl which is unsubstituted or is substituted with from 1 to 3 substituents selected from:
alkyl having from 1 to 6 carbon atoms and which is straight or branched;
alkoxy having from 1 to 6 carbon atoms and which is straight or branched,
phenoxy,
hydroxy,
fluorine,
chlorine,
bromine,
nitro,
trifluoromethyl,
—COOH,
—COO alkyl wherein alkyl has from one to four carbon atoms,
—$NR_3R_4$ wherein $R_3$ and $R_4$ have the meanings defined above; and
(c) the group

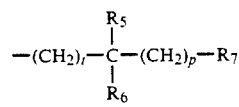

wherein t is zero to 4;
p is zero to 4 with the proviso that the sum of t and p is not greater than 5;
$R_5$ and $R_6$ are independently selected from hydrogen or alkyl having from 1 to 6 carbon atoms, or when $R_5$ is hydrogen, $R_6$ can be selected from the groups defined for $R_7$ and $R_7$ is phenyl or phenyl substituted with from 1 to 3 substituents selected from straight or branched alkyl having from 1 to 6 carbon atoms, straight or branched alkoxy having from 1 to 4 carbon atoms, straight or branched thioalkoxy having from 1 to 4 carbon atoms, phenoxy, hydroxy, fluorine, chlorine, bromine, nitro, trifluoromethyl, —COOH, —COO alkyl wherein alkyl has from one to four carbon atoms or $NR_3R_4$ wherein $R_3$ and $R_4$ have the meanings defined above;

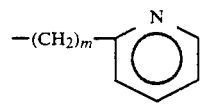
(d)

wherein m is an integer of from zero to three;
wherein $R_2$ is selected from

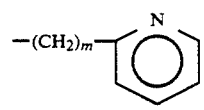
(a)

wherein m is an integer of from zero to three;

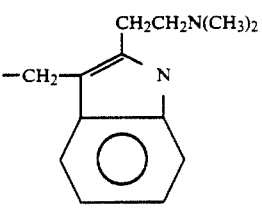
(b)

(c) —(CH$_2$)$_q$—O—Ph wherein q is an integer of from 2 to 10 and Ph is phenyl or phenyl substituted with from 1 to 3 substituents selected from straight or branched alkyl having from 1 to 6 carbon atoms, straight or branched alkoxy having from 1 to 6 carbon atoms, straight or branched thioalkoxy having from 1 to 6 carbon atoms, phenoxy, hydroxy, fluorine, chlorine, bromine, nitro, trifluoromethyl, or NR$_3$R$_4$ wherein R$_3$ and R$_4$ have the meanings defined above;

(d) a straight or branched hydrocarbon chain having from 1 to 20 carbon atoms and which is saturated or contains from 1 to 3 double bonds;

(e) the group

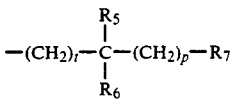

wherein t p, R$_5$, R$_6$, and R$_7$ have the meanings defined above; or a pharmaceutically acceptable salt thereof.

The compound N-[2,6-bis(1-methylethyl) phenyl]-2,3,4,5,6,7,8,9,10,11,12,13-dodecahydro-1-oxo-1H-cyclopentacyclododecene-2-carboxamide and pharmaceutically acceptable salts thereof are also included in the scope of this invention.

DETAILED DESCRIPTION OF THE INVENTION

The compounds of the present invention provide a novel class of cyclic beta-ketoamides which are ACAT inhibitors, rendering them useful in treating hypercholesterolemia and atherosclerosis.

Illustrative examples of a straight or branched saturated hydrocarbon chain having from 1 to 20 carbon atoms include methyl, ethyl, n-propyl, isopropyl, n-butyl, isobutyl, tert-butyl, n-pentyl, isopentyl, n-hexyl, n-heptyl, n-octyl, n-undecyl, n-dodecyl, n-hexadecyl, 2,2-dimethyldodecyl, 2-ethyltetradecyl, and n-octadecyl groups.

Illustrative examples of a straight or branched hydrocarbon chain having from 1 to 20 carbon atoms and having from 1 to 3 double bonds are ethenyl, 2-propenyl, 2-butenyl, 3-pentenyl, 2-octenyl, 5-nonenyl, 4-undecenyl, 5-heptadecenyl, 3-octadecenyl, 9-octadecenyl, 2,2-dimethyl-11-eicosenyl, 9,12-octadecadienyl, and hexadecenyl.

Straight or branched alkoxy groups having from 1 to 6 carbon atoms include, for example, methoxy, ethoxy, n-propoxy, tert-butoxy, and pentyloxy.

Illustrative of straight or branched thioalkoxy groups having from 1 to 6 carbon atoms are methylthio, ethylthio, n-propylthio, isopropylthio, and butylthio. The thioalkoxy group may also be referred to as alkylthio.

Illustrative examples of straight or branched alkyl groups having from 1 to 4 or from 1 to 6 carbon atoms include methyl, ethyl, n-propyl, isopropyl, n-butyl, tert-butyl, pentyl, and hexyl.

The various phenyl moieties of the compounds of general Formula I may be unsubstituted or substituted with from 1 to 3 substituents, in which latter case the substituents may be the same or different and may be attached to any available position on the aromatic moiety.

Preferred compounds of this invention are those of Formula I wherein Ar is phenyl substituted with alkyl and more preferably disubstituted in the 2 and 6 positions. Compounds wherein n is 1 to 3 are also preferred as are compounds wherein Y is oxygen.

Pharmaceutically acceptable salts of the compounds of Formula I are also included as a part of the present invention.

The base salts may be generated from compounds of Formula I by reaction of the latter with one equivalent of a suitable nontoxic, pharmaceutically acceptable base followed by evaporation of the solvent employed for the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well known to practitioners of the pharmaceutical formulation arts. See, for example, Stephen N. Berge, et al, J Pharm Sci 16, 1-19 (1977).

Suitable acids for forming acid salts of the compounds of this invention containing a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

Certain compounds of the present invention may also exist in different stereoisomeric forms by virtue of the presence of asymmetric centers in the compound. The present invention contemplates all stereoisomeric forms of the compounds as well as mixtures thereof, including racemic mixtures. Individual stereoisomers may be obtained, if desired, by methods known in the art as, for example, the separation of stereoisomers on chiral chromatographic columns.

Further, the compounds of this invention may exist in unsolvated as well as solvated forms with pharmaceutically acceptable solvents such as water, ethanol, and the like. In general, the solvated forms are considered equivalent to the unsolvated forms for the purposes of this invention.

As shown by the data presented below in Table 1, the compounds of the present invention are potent inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in F. J. Field and R. G. Salone, Biochemica et Biophysica 712:557-570 (1982). The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes.

The compounds are also evaluated in an in vivo screen, designated APCC, wherein male Sprague-Dawley rats (200 to 225 g) are randomly divided into treatment groups and dosed at 4 PM with either vehicle (CMC/Tween) or suspensions of compounds in vehicle. The normal chow diet is then replaced with the PCC diet with either 1% or 0.5% cholic acid, as indicated. The rats consume this diet ad libitum during the night and are sacrificed at 8 AM to obtain blood samples for cholesterol analysis using standard procedures. Statistical differences between mean cholesterol values for the same vehicle are determined using analysis of variance followed by Fisher's least significant test.

TABLE 1

| Compound of Example | $IC_{50}$ ($\mu M$) |
| --- | --- |
| 1 | >1 |
| 2 | 1.0 |
| 3 | >1 |
| 4 | 0.259 |
| 5 | 0.94 |
| 6 | 0.072 |

In therapeutic use as agents for treating hypercholesterolemia or atherosclerosis, the compounds of Formula I are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about 5% to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral administration, or suspensions and emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methylcellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The compounds of this invention are prepared as depicted in the attached Chart I of Scheme A. A cycloalkanone (1) is treated with lithium diisopropylamide to form a lithio enolate which is treated with an appropriate aryl isocyanate or thioisocyanate of the formula ArNCY to give the compounds of Formula I. The cycloalkanone (1) is commercially available or can be prepared as shown in Scheme B of Chart I by treating a cycloalkanone (2) with a base such as sodium hydride and alkylating with an appropriate agent of the formula $R_1Cl$ or $R_2Cl$ as generally described by H. House et al., Organic Syntheses 52, p. 39. In Chart I the various symbols n, $R_1$, $R_2$, Ar, and Y have the meanings defined in Formula I.

EXAMPLE 1

Preparation of
N-2,6-bis(1-methylethyl)phenyl]-2-oxo-3-phenyl-3-(2-pyridinyl)cyclopentanecarboxamide To a cooled solution (−78° C.) of diisopropylamine (0.37 g, 0.003 mol) in 16 mL ether, n-BuLi (0.003 mol) was added dropwise followed by 8 mL ether. After stirring for 5 minutes at −78° C. under a nitrogen atmosphere, a solution of 2-phenyl-2-(2 pyridyl)-cyclopentanone (0.90 g, 0.003 mol, prepared from the alkylation of cyclopentanone with chlorobenzene, 2-chloropyridine, and sodium hydride) in 4 mL ether was added dropwise and the resulting solution was stirred for 20 minutes at −78° C. A solution of 2,6-diisopropylphenyl isocyanate in 4 mL ether was then added dropwise and the reaction mixture was allowed to gradually warm to room temperature and stir for 16 hours under a nitrogen atmosphere (J. F. Wolfe, et al, Synthetic Communications 17, 13 (1987)). The reaction mixture was then quenched with a saturated solution of ammonium chloride and extracted with methylene chloride. The layers were separated and the organic layer was washed two times with water, dried ($Na_2SO_4$) and concentrated in vacuo (30° C.) to afford a residue. Purification by flash chromatography (silica gel, 30% EtOAc/hexane) yielded 0.70 g (0.001 mol, 43%) of the desired product.

MS: 441.84 ($MH^+$), 440.81 ($M^+$).

EXAMPLE 2

Preparation of N-[2,6 bis(1-methylethyl)phenyl]-2-oxo-3-phenyl-3-(2-pyridinyl)cyclohexanecarboxamide The title compound was prepared from 2-phenyl-2-(2-pyridyl)-cyclohexanone (4.50 g, 0.017 mol, prepared from the alkylation of 2-phenylcyclohexanone with 2-chloropyridine and sodium hydride), 2,6-diisopropylphenyl isocyanate (3.60 g, 0.017 mol), and lithium diisopropylamide (0.017 mol) using the procedure described in Example 1.

MS: 455.03 (MH+), 454.03 (M+).

EXAMPLE 3

Preparation of N-[2,6 bis(1-methylethyl) phenyl-3-[2-[2-(dimethylamino)ethyl]-1-methyl-1H-indol-3-yl]methyl]-2-oxo-3-phenylcyclohexanecarboxamide The title compound, mp 125°–126° C., was prepared from 2-[[2-[2-(dimethylamino)ethyl]-1-methyl-1H -indol-3yl]methyl]-2-phenylcyclohexanone monohydrochloride (CAS Reg. No. 58981-85-4; the free amine was obtained by treating the monohydrochloride with 1N NaOH aqueous solution, extracting with ether, and drying the ether layer with $Na_2SO_4$, 2.40 g, 0.006 mol), 2,6-diisopropylphenyl isocyanate (1.20 g, 0.006 mol), and lithium diisopropylamide (0.006 mol) using the procedure described in Example 1.

EXAMPLE 4

Preparation of N-[2,6-bis(1 methylethyl) phenyl]-2-oxo-3-phenyl-3-(2-pyridinylmethyl)cyclohexanecarboxamide The title compound, mp 164°–166° C., was prepared from 2-phenyl-2-(2-pyridylmethyl)cyclohexanone (3.00 g, 0.011 mol, prepared from the alkylation of 2-phenylcyclohexanone with 2-picolyl chloride and sodium hydride), 2,6-diisopropylphenyl isocyanate (2.29 g, 0.011 mol) and lithium diisopropyl amide (0.011 mol) using the procedure described in Example 1.

EXAMPLE 5

Preparation of N-[2,6-bis(1-methylethyl) phenyl]-2-oxo-3,3-bis(2-pyridinylmethyl)cyclohexanecarboxamide The title compound, mp 70°–73° C., was prepared from 2,2-bis(2-pyridylmethyl)cyclohexanone (2.50 g, 0.008 mol, prepared from the alkylation of cyclohexanone with 2 picolyl chloride and sodium hydride), 2,6-diisopropylphenyl isocyanate (1.80 g, 0.008 mol) and lithium diisopropylamide (0.008 mol) using the procedure described in Example 1.

EXAMPLE 6

Preparation of N-[2,6-bis (1-methylethyl)phenyl]-2-oxo-3-(5-phenoxypentyl)-3-phenylcyclohexanecarboxamide Step A: Preparation of 2 (5-phenoxypentyl)-2-phenylcyclohexanone To a mixture of 5 phenoxy pentyl bromide (122.0 g, 0.5 mol) and 2-phenylcyclohexanone (104.4 g, 0.6 mol) in 1.5 L THF, NaH (0.55 mol, 24.0 g) was added portionwise, keeping the temperature between 25° to 30° C. After most of the $H_2$ evolution had ceased, the reaction mixture was heated to reflux for 16 hours under a $N_2$ atmosphere. After cooling to room temperature, 50 mL isopropanol was added and the mixture was concentrated in vacuo to half its volume. This residue was diluted with 2 L ether and 1 L $H_2O$. The layers were separated and the aqueous layer was washed one time with 500 mL ether. The combined organic layers were washed two times each with 500 mL $H_2O$, dried ($MgSO_4$), and concentrated in vacuo to give a solid. Recrystallization from petroleum ether yielded 27.5 g (16.4%), mp 69°–72° C., of the desired product.

Step B: Preparation of N-[2,6-bis(1-methylethyl)-phenyl]-2-oxo-3-(5-phenoxypentyl)-3-phenyl-cyclohexane carboxamide The title compound, mp 150°–153° C., was prepared from 2-(5-phenoxypentyl)-2-phenylcyclohexanone (2.50 g, 0.007 mol), 2,6 diisopropylphenyl isocyanate (1.42 g, 0.007 mol), and lithium diisopropylamide (0.007 mol) using the procedure described in Example 1.

EXAMPLE 7

Preparation of N-[2,6-bis(1-methylethyl) phenyl]-2,3,4,5,6,7,8,9,10,11,12,13-dodecahydro-1-oxo-1H-cyclopentacyclododecene-2-carboxamide The title compound, mp 225°–229° C., was prepared from bicyclo[10.3.0]pentadec-12(1)-en-13 one (5.0 g, 0.022 mol), 2,6-diisopropylphenyl isocyanate (4.60 g, 0.022 mol), and lithium diisopropylamide (0.022 mol) using the procedure described in Example 1.

CHART 1
SCHEME A:

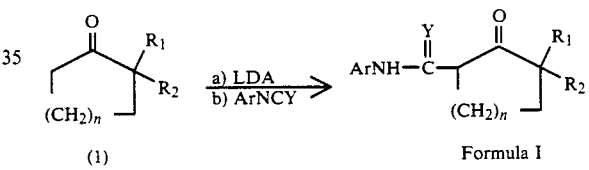

SCHEME B:

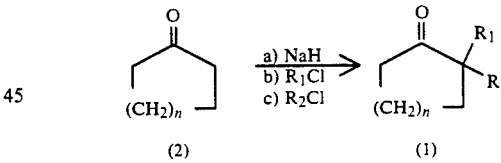

I claim:
1. A compound of the formula

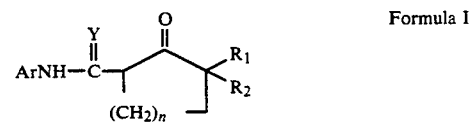

Formula I wherein Y is oxygen or sulfur;
wherein Ar is selected from:
(a) phenyl which is unsubstituted or is substituted with from 1 to 3 substituents selected from:
alkyl having from 1 to 6 carbon atoms and which is straight or branched,
alkoxy having from 1 to 6 carbon atoms and which is straight or branched,
phenoxy,
hydroxy,
fluorine, chlorine,
bromine,
nitro,
trifluoromethyl,
—COOH,
—COOalkyl wherein alkyl has from 1 to 4 carbon atoms,
—NR$_3$R$_4$ wherein R$_3$ and R$_4$ are independently hydrogen or alkyl of from 1 to 4 carbon atoms;
wherein n is an integer of from 0 to 3;
wherein R$_1$ is selected from
 (a) hydrogen;
 (b) phenyl which is unsubstituted or is substituted with from 1 to 3 substituents selected from:
  alkyl having from 1 to 6 carbon atoms and which is straight or branched;
  alkoxy having from 1 to 6 carbon atoms and which is straight or branched,
  phenoxy,
  hydroxy,
  fluorine,
  chlorine,
  bromine,
  nitro,
  trifluoromethyl,
  —COOH,
  —COO alkyl wherein alkyl has from one to four carbon atoms,
  —NR$_3$R$_4$ wherein R$_3$ and R$_4$ have the meanings defined above; and
 (c) the group

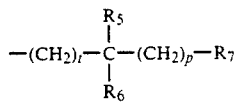

wherein t is zero to 4;
 p is zero to 4 with the proviso that the sum of t and p is not greater than 5;
 R$_5$ and R$_6$ are independently selected from hydrogen or alkyl having from 1 to 6 carbon atoms, or when R$_5$ is hydrogen, R$_6$ can be selected from the groups defined for R$_7$ and R$_7$ is phenyl or phenyl substituted with from 1 to 3 substituents selected from straight or branched alkyl having from 1 to 6 carbon atoms, straight or branched alkoxy having from 1 to 4 carbon atoms, straight or branched thioalkoxy having from 1 to 4 carbon atoms, phenoxy, hydroxy, fluorine, chlorine, bromine, nitro, trifluoromethyl, —COOH, —COO alkyl wherein alkyl has from one to four carbon atoms, or NR$_3$R$_4$ wherein R$_3$ and R$_4$ have the meanings defined above;
wherein R$_2$ is selected from

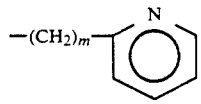

wherein m is an integer from zero to three.

2. A compound of claim 1 wherein n is 1 to 3.

3. A compound of claim 2 wherein Y is oxygen.

4. A compound of claim 3 wherein Ar is phenyl substituted with alkyl having from 1 to 6 carbon atoms and is straight or branched.

5. A compound of claim 4 wherein phenyl is disubstituted in the 2 and 6 positions.

6. A compound of claim 5 which is
N-[2,6-bis(1-methylethyl)phenyl]-2-oxo-3-phenyl-3-(2-pyridinyl)cyclopentanecarboxamide;
N-[2,6-bis(1-methylethyl)phenyl]-2-oxo-3-phenyl-3-(2-pyridinyl)cyclohexanecarboxamide;
N-[2,6-bis(1 methylethyl)phenyl]-2-oxo-3-phenyl-3-(2 pyridinylmethyl)cyclohexanecarboxamide.

7. A pharmaceutical composition which comprises a compound of claim 1 and a pharmaceutically acceptable carrier.

8. A method of lowering the cholesterol levels in a patient in need thereof which comprises administering to said patient an effective amount of a compound of claim 1.

* * * * *